United States Patent
Tanaka

(10) Patent No.: US 9,459,036 B2
(45) Date of Patent: Oct. 4, 2016

(54) SAMPLE COOLING DEVICE

(71) Applicant: SHIMADZU CORPORATION, Kyoto (JP)

(72) Inventor: Shinji Tanaka, Osaka (JP)

(73) Assignee: SHIMADZU CORPORATION, Kyoto (JP)

(*) Notice: Subject to any disclaimer, the term of this patent is extended or adjusted under 35 U.S.C. 154(b) by 415 days.

(21) Appl. No.: 14/196,302

(22) Filed: Mar. 4, 2014

(65) Prior Publication Data

US 2014/0250938 A1    Sep. 11, 2014

(30) Foreign Application Priority Data

Mar. 8, 2013  (JP) ................. 2013-046516

(51) Int. Cl.

| | | |
|---|---|---|
| F25B 21/02 | (2006.01) | |
| F25D 11/00 | (2006.01) | |
| G01N 25/14 | (2006.01) | |
| F25D 21/04 | (2006.01) | |
| F25D 17/08 | (2006.01) | |
| A01N 1/02 | (2006.01) | |

(52) U.S. Cl.
CPC ............ *F25D 11/00* (2013.01); *A01N 1/0252* (2013.01); *F25B 21/02* (2013.01); *F25D 21/04* (2013.01); *G01N 25/145* (2013.01); *A01N 1/0242* (2013.01); *F25D 17/08* (2013.01); *F25D 2317/0411* (2013.01)

(58) Field of Classification Search
USPC ............................................. 62/62
See application file for complete search history.

(56) References Cited

U.S. PATENT DOCUMENTS 6,170,267 B1 *  1/2001  Kitaoka ................ F25D 31/007
                                                         62/3.6

FOREIGN PATENT DOCUMENTS

| JP | 2000-074802 A | 3/2000 |
|---|---|---|
| JP | 2001-012839 A | 1/2001 |
| JP | 2005-233867 A | 9/2005 |

* cited by examiner

*Primary Examiner* — Orlando Aviles Bosques
(74) *Attorney, Agent, or Firm* — Westerman, Hattori, Daniels & Adrian, LLP

(57) ABSTRACT

A sample cooling device is provided with, inside a sample storage which stores therein a sample rack, a first heat transfer member arranged at a position in contact with the sample rack, a second heat transfer member which cools the inside of the sample storage, and a condensate discharge mechanism which discharges condensate condensing on the second heat transfer member to the outside of the sample storage. An internal space of the sample storage is not sealed due to the existence of a leak path for air formed between the inside and the outside of the sample storage, the leak path including at least the channel. The sample storage includes an outside air introduction unit which forcibly blows the outside air into the internal space so that the pressure inside the sample storage becomes higher than the outside pressure thereof. The position and the direction of an outside air outlet of the outside air introduction unit inside the sample storage are set so that the outside air blown into the sample storage directly heads for the second heat transfer member.

5 Claims, 2 Drawing Sheets

SAMPLE COOLING DEVICE

BACKGROUND OF THE INVENTION

1. Field of the Invention

The present invention relates to a sample cooling device which cools a sample before analysis in an analyzer such as a liquid chromatograph analyzer.

2. Description of the Related Art

A sample cooling system of a sample cooling device which cools a sample before analysis includes a direct cooling system and an air cooling system. In the direct cooling system, a sample rack in which a sample container which stores therein a sample is set is placed on a sample rack placing unit that has been cooled to thereby directly cool the sample container through the sample rack (see Japanese Unexamined Patent Application Publication No. 2000-74802 and Japanese Unexamined Patent Application Publication No. 2001-12839). In the air cooling system, air inside a sample storage is cooled and circulated by a cooling Peltier element to thereby cool the entire air inside the sample storage (see Japanese Unexamined Patent Application Publication No. 2005-233867). The sample rack placing unit of the direct cooling system includes a sample rack cooling plate for directly placing and cooling the sample rack thereon, a Peltier element which cools the sample rack cooling plate, a heat dissipation fin which dissipates heat from the Peltier element, and a heat insulating material which blocks thermal conduction from components other than the Peltier element. The sample rack cooling plate is placed inside the sample storage, and the heat dissipation fin is placed outside the sample storage.

Since the direct cooling system can directly cool only the sample rack, the time required to reach a desired cooling temperature is advantageously short (that is, the cooling efficiency is excellent). However, on the other hand, since only the sample rack is cooled, moisture contained in the air inside the storage condenses on the cooled sample rack. In order to prevent such a problem, a dehumidification mechanism is provided. In the dehumidification mechanism, another Peltier element (hereinbelow, referred to as a dehumidification Peltier element) is provided to forcibly cause the moisture contained in the air inside the storage to condense on a dehumidification cooling plate which is cooled by the dehumidification Peltier element. Further, the condensate is collected in a tray, and the collected condensate is discharged to the outside of the storage through a tube or the like to thereby dehumidify the air inside the storage.

Such a sample cooling device includes one that constitutes a sample injection device of an analyzer such as a liquid chromatograph analyzer and one that is used for storing a sample separately from the sample injection device. The present invention is directed to both of the sample cooling devices.

The sample cooling device is designed so that the airtightness inside the storage of the device becomes as high as possible in order to prevent condensation in a sample rack cooling unit. However, when the sample cooing device constitutes the sample injection device, a mechanism that moves and cleans a sampling needle for sample injection is provided inside the storage of the device. Therefore, inside the storage are formed: a hole for discharging therethrough a cleaning liquid; a hole for discharging therethrough a leaking liquid; and a gap as a leak path such as a notch for passing therethrough a channel pipe or a wire. The leaking liquid is generated, for example, when a channel switching valve for introducing a sample for analysis into an analysis channel is exhausted, and the leakage of a mobile phase solvent thereby occurs.

Also in the sample cooling device that does not constitute the sample injection device, an outlet through which condensate condensing on the dehumidification cooling plate (heat transfer member) which is cooled by the dehumidification Peltier element is discharged to the outside of the storage serves as the leak path.

The inside of the storage of the sample cooling device communicates with the outside air through such a leak path, and therefore, cannot be completely sealed. Therefore, even when the dehumidification mechanism operates, the outside air flows into the storage from the outside thereof through the leak path, and the humidity inside the storage thereby increases. As a result, condensation may occur in the sample rack cooling unit, the sample rack, and the sample container.

SUMMARY OF THE INVENTION

The present invention is directed to prevent the occurrence of condensation in a sample container due to the outside air flowing into a storage from the outside thereof through a leak path.

In the present invention, the pressure inside a storage is made to be a positive pressure that is higher than the outside pressure thereof by forcibly introducing the outside air into the storage, thereby preventing the outside air from flowing into the storage from the outside thereof through a leak path. In addition, in order to remove moisture contained in the outside air flowing into the storage, the outside air is allowed to directly head for a dehumidification heat transfer member.

Specifically, according to one aspect of the present invention, a sample cooling device includes: a sample storage which stores therein a sample rack, the sample rack holding a sample container in which a sample is put; a first temperature regulation mechanism which includes a first heat transfer member arranged at a position in contact with the sample rack stored inside the sample storage and a first cooler which cools the sample rack to a temperature equal to or lower than a room temperature through the first heat transfer member; a second temperature regulation mechanism which includes a second heat transfer member arranged at a position separately from the first heat transfer member inside the sample storage and a second cooler which cools the inside of the sample storage to a temperature equal to or lower than a room temperature through the second heat transfer member; and a condensate discharge mechanism which includes a condensate collection tray arranged at a position for collecting condensate condensing on the second heat transfer member and a channel for discharging therethrough the condensate collected in the condensate collection tray to the outside of the sample storage.

An internal space of the sample storage is not sealed due to the existence of a leak path for air formed between the inside and the outside of the sample storage, the leak path including at least a channel for discharging therethrough condensate to the outside of the sample storage. Further, the sample storage includes an outside air introduction unit which forcibly blows the outside air into the internal space so that the pressure inside the sample storage becomes higher than the outside pressure thereof. The position and the direction of an outside air outlet of the outside air introduction unit inside the sample storage are set so that the outside air blown into the sample storage directly heads for the second heat transfer member.

According to one aspect of the present invention, the sample cooling device constitutes a sample injection device. In such a case, the sample cooling device includes a sample inlet of an analyzer, a sampling needle which sucks a sample from a sample container held in the sample rack and injects the sample into the sample inlet, and a cleaning liquid discharge port for discharging therethrough a cleaning liquid used for cleaning the sampling needle. The sample inlet, the sampling needle, and the cleaning liquid discharge port are arranged inside the sample storage. Further, the leak path also includes an outlet of the cleaning liquid discharge port.

In order to allow the outside air blown into the sample storage to directly head for the second heat transfer member, the sample cooling device preferably includes a guide plate which directs the outside air blown into the sample storage through the outside air outlet to the second heat transfer member.

Further, in order to allow the outside air blown into the sample storage to directly head for the second heat transfer member, it is also preferred that the second heat transfer member include a plurality of metal plates which are arranged in parallel to the flow of the outside air blown into the sample storage through the outside air outlet.

The outside air introduction unit is required to have an air feeding mechanism for blowing the outside air into the internal space. As an embodiment, the outside air introduction unit may be provided with a dedicated air feeding mechanism.

On the other hand, Peltier elements may be used as the first cooler and the second cooler. When using the Peltier elements, heat dissipation fins for the respective Peltier elements and air feeding mechanisms for feeding air for heat dissipation to the respective heat dissipation fins are provided outside the sample storage. Therefore, as another form of the air feeding mechanism for blowing the outside air into the internal space, either one of the air feeding mechanisms for the respective heat dissipation fins can also serve as the air feeding mechanism for blowing the outside air into the internal space. By using one air feeding mechanism for two purposes in this manner, it is possible to simplify the configuration of the sample cooling device to thereby reduce a cost thereof.

In the present invention, even with the structure in which the internal space of the sample storage is not sealed, the pressure inside the sample storage becomes a positive pressure by providing the outside air introduction unit. As a result, the inflow of the outside air into the sample storage from the outside thereof through the leak path is reduced.

Further, since the position and the direction of the outside air outlet of the outside air introduction unit are set so that the outside air blown into the sample storage directly heads for the second heat transfer member, the outside air flowing into the sample storage is immediately dehumidified by the second heat transfer member. Therefore, the humidity inside the sample storage does not increase.

DETAILED DESCRIPTION OF THE PREFERRED EMBODIMENT

Figure 1:
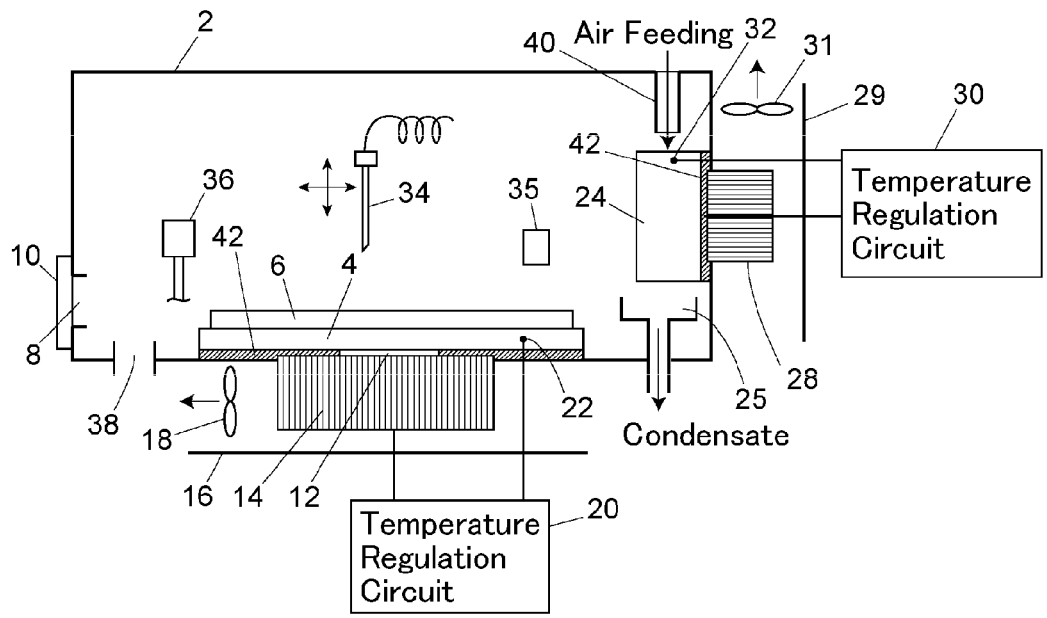
FIG. 1 is a schematic cross-sectional view illustrating an embodiment.

An embodiment of the present invention is illustrated in FIG. 1.

A sample cooling plate 4 as a first heat transfer member is provided in a lower part of a sample storage 2. A sample rack 6 is placed on the sample cooling plate 4. A plurality of sample containers, each of which stores therein a liquid sample, are put into the sample rack 6 in an aligned manner. Each of the sample containers is, for example, a small bottle made of glass. A sample rack insertion port 8 is provided on the front of the sample storage 2 (the left side in the drawing) for inserting and taking out the sample rack 6 into and from the sample storage 2. The sample rack insertion port 8 is closed by an openable/closable lid 10. The sample rack 6 is made of, for example, aluminum in order to improve the thermal conductivity thereof, and has a plurality of holes for inserting thereinto the sample containers.

In order to cool the sample rack 6 which is placed on the sample cooling plate 4, a Peltier element 12 as a first cooler is provided in contact with the sample cooling plate 4. In order to dissipate heat of the Peltier element 12, a heat dissipation fin 14 is provided outside the sample storage 2. In order to feed air to the heat dissipation fin 14 for heat dissipation, the heat dissipation fin 14 is arranged inside a duct 16, and a fan 18 for air feeding is provided in the duct 16.

In order to control the temperature of the sample cooling plate 4, a temperature regulation circuit 20 and a temperature sensor 22 are provided. The temperature sensor 22 is embedded in the sample cooling plate 4 or attached in contact with the sample cooling plate 4 in order to detect the temperature of the sample cooling plate 4. The temperature regulation circuit 20 takes in a temperature detected by the temperature sensor 22, and controls the amount of current supplied to the Peltier element 12 so that the sample cooling plate 4 has a predetermined temperature.

The sample cooling plate 4, the Peltier element 12, the heat dissipation fin 14, the temperature regulation circuit 20, and the temperature sensor 22 together constitute a first temperature regulation mechanism.

A dehumidification cooling plate 24 as a second heat transfer member is arranged at a position separately from the sample cooling plate 4 inside the sample storage 2 in order to remove moisture contained in the air inside the sample storage 2. Although the dehumidification cooling plate 24 is arranged on the right side inner surface of the sample storage 2 in the drawing, the position of the dehumidification cooling plate 24 is not particularly limited to the illustrated position. In order to cool the dehumidification cooling plate 24 to a predetermined temperature, a dehumidification Peltier element 26 as a second cooler is arranged in contact with the dehumidification cooling plate 24. A heat dissipation fin 28 for the Peltier element 2 is provided outside the sample storage 2. In order to feed air to the heat dissipation fin 28 for heat dissipation, the heat dissipation fin 28 is arranged inside a duct 29, and a fan 31 for air feeding is provided in the duct 29.

In order to control the temperature of the dehumidification cooling plate 24, a temperature regulation circuit 30 and a temperature sensor 32 are provided. The temperature sensor 32 is embedded in the dehumidification cooling plate 24 or attached in contact with the dehumidification cooling plate 24 in order to detect the temperature of the dehumidification cooling plate 24. The temperature regulation circuit 30 takes in a temperature detected by the temperature sensor 32, and controls the amount of current supplied to the Peltier element 26 so that the dehumidification cooling plate 24 has a predetermined temperature.

The dehumidification cooling plate 24, the Peltier element 26, the heat dissipation fin 28, the temperature regulation circuit 30, and the temperature sensor 32 together constitute a second temperature regulation mechanism.

Each of the sample cooling plate 4 and the dehumidification cooling plate 24 includes metal having a high thermal conductivity such as aluminum, copper, and stainless steel.

The sample cooling device of the present embodiment constitutes a sample injection device which is a liquid chromatograph autosampler. Therefore, a sample inlet 35 for liquid chromatograph, a sampling needle 34 for sucking a sample from a sample container put in the sample rack 6 and injecting the sample into the sample inlet 35 for liquid chromatograph, and a cleaning liquid discharge port 36 for discharging therethrough a cleaning liquid that has been used for cleaning the sampling needle 34 are arranged inside the sample storage 2. The sampling needle 34 is moved by a conveyance mechanism (not shown) among the positions of a predetermined sample container, the sample inlet 35, and the cleaning liquid discharge port 36.

A pipe that communicates with the cleaning liquid discharge port 36 is led out of the sample storage 2. In addition to the cleaning liquid discharge pipe communicating with the cleaning liquid discharge port 36, an outlet for discharging therethrough a leaking liquid, a notch for passing therethrough a wire or a pipe, and the like serve as leak paths of the sample storage 2. These leak paths are schematically illustrated in a collected manner as a leak path 38 in the drawings. Therefore, the leak path 38 does not indicate that only a single leak path exists on the illustrated position. In this manner, since the leak path 38 exists in the sample storage 2, it is not possible to completely seal an internal space of the sample storage 2.

When the outside air enters the inside of the sample storage 2 through the leak path 38, moisture is also introduced into the sample storage 2 along with the outside air. As a result, the humidity inside the sample storage 2 increases. In order to prevent such a situation, in the present embodiment, an outside air introduction unit 40 is provided in the sample storage 2 to maintain the pressure inside the sample storage 2 at a positive pressure that is higher in some degree than the atmospheric pressure around the sample storage 2.

The outside air fed through the outside air introduction unit 40 is ambient air, and therefore contains moisture. Thus, if the outside air is directly blown into the sample storage 2, the humidity inside the sample storage 2 increases. Therefore, in the present embodiment, the position and the direction of an outside air outlet of the outside air introduction unit 40 are set so that the outside air blown into the sample storage 2 directly heads for the dehumidification cooling plate 24. Specifically, the dehumidification cooling plate 24 is arranged on an upper part of the inner side surface of the sample storage 2. Further, the outside air outlet of the outside air introduction unit 40 is arranged so as to face the dehumidification cooling plate 24. In addition, a distance between the outside air outlet of the outside air introduction unit 40 and the dehumidification cooling plate 24 is set to be as short as possible, for example, set at one to several centimeters.

A tray 25 which receives condensate condensing on the dehumidification cooling plate 24 is provided below the dehumidification cooling plate 24. A tube 27 for discharging therethrough the condensate received in the tray 25 is connected to the tray 25. An outlet of the tube 27 is also included in the leak path 38.

A heat insulating material 42 is provided between the sample cooling plate 4 and the wall surface of the sample storage 2 to achieve thermal insulation of the sample cooling plate 4. In a direct cooling system, only the sample cooling plate 4 is required to be thermally insulated, and components other than the sample cooling plate 4 are therefore not necessarily thermally insulated. In the present embodiment, in order to improve the cooling efficiency of the dehumidification cooling plate 24, another heat insulating material 42 is provided between the dehumidification cooling plate 24 and the wall surface of the sample storage 2. Further, almost the entire inner surface of the sample storage 2 may be covered by a heat insulating material.

In order to blow the outside air into the sample storage 2 through the outside air outlet of the outside air introduction unit 40, the outside air introduction unit 40 is provided with a mechanism for feeding the outside air into the sample storage 2, the mechanism being arranged outside the sample storage 2. An example of the mechanism is a dedicated fan which is provided in the outside air introduction unit 40. The flow rate of the outside air to be fed into the sample storage 2 through the outside air introduction unit 40 may be small as long as the pressure inside the sample storage 2 can be made to be a positive pressure that is slightly higher than the atmospheric pressure outside the sample storage 2. Therefore, even when the dedicated fan is provided, a small fan is enough as the dedicated fan.

Figure 2:
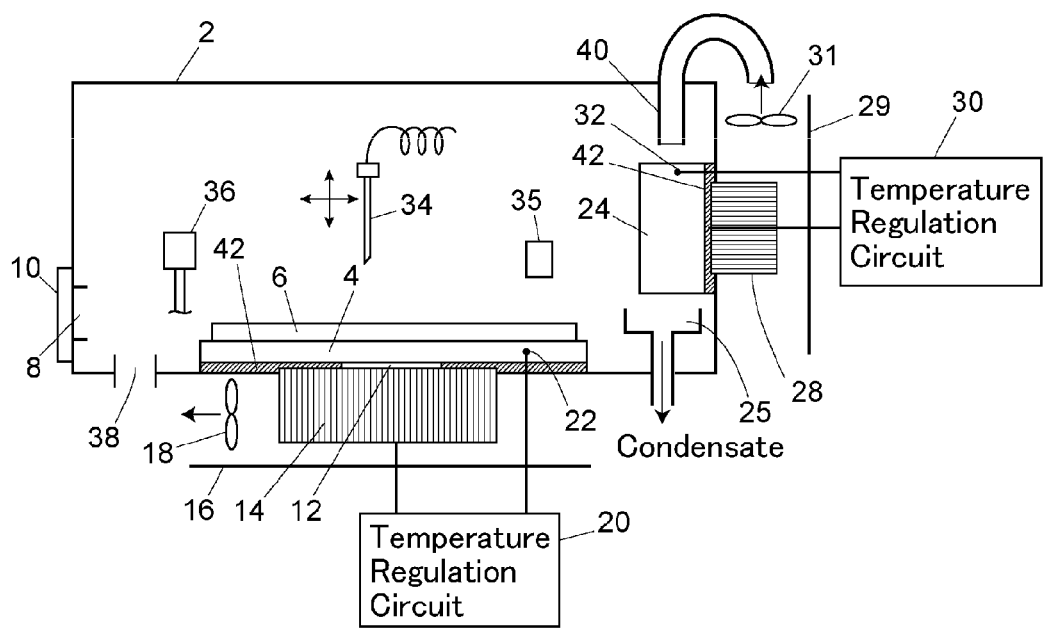
FIG. 2 is a schematic cross-sectional view illustrating an example of a mechanism for blowing the outside air into a sample storage through an outside air introduction unit in an embodiment.

Another example of the mechanism for blowing the outside air into the sample storage 2 through the outside air introduction unit 40 is illustrated in FIG. 2. This example uses the fan 31 for heat dissipation of the heat dissipation fin 28 for the Peltier element 28 as the mechanism. One end of a pipe 52 is arranged on an outlet of the duct 29, and the other end of the pipe 52 is connected to the outside air introduction unit 40. By virtue of the pipe 52, a part of air flowing through the duct 29 is blown into the sample storage 2 through the outside air introduction unit 40.

Yet another example of the mechanism for blowing the outside air into the sample storage 2 through the outside air introduction unit 40 uses the fan 8 for heat dissipation of the heat dissipation fin 14 for the Peltier element 12. In this example, one end of the pipe 52 is arranged on an outlet of the duct 16, and the other end of the pipe 52 is connected to the outside air introduction unit 40.

Figure 3:
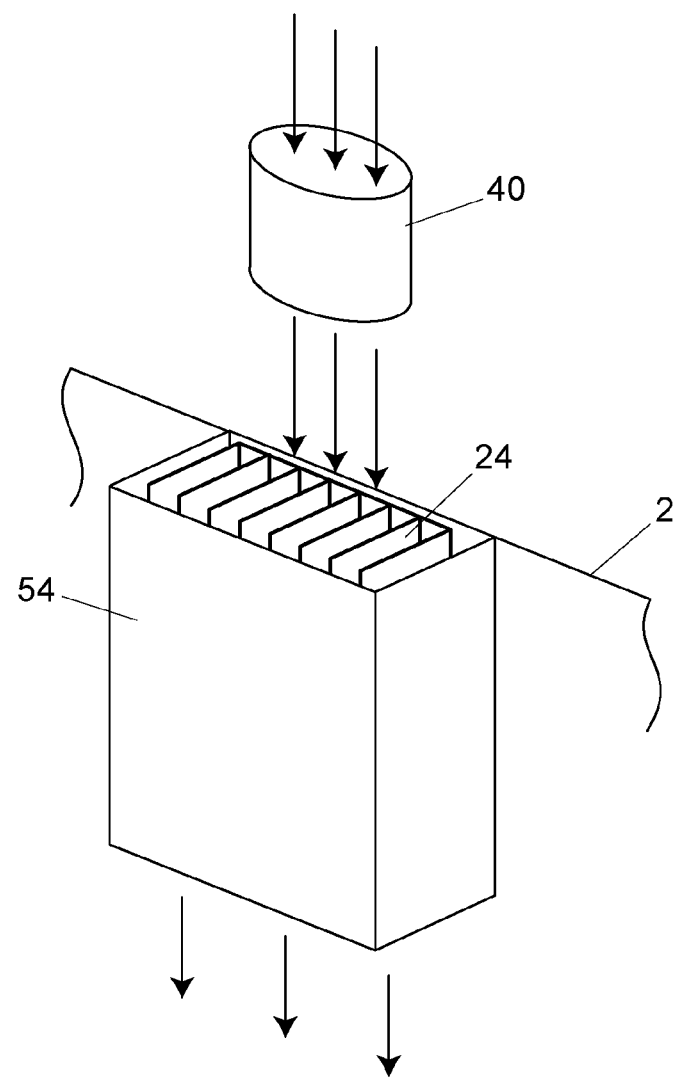
FIG. 3 is a schematic perspective view illustrating a dehumidification cooling plate and a guide plate in an embodiment.

A preferred embodiment of the dehumidification cooling plate 24 which promptly causes condensation of moisture contained in the outside air fed through the outside air introduction unit 40 to remove the moisture is illustrated in FIG. 3. The outside air outlet 40 of the outside air introduction unit 40 is arranged above the cooling plate 24 so as to face the cooling plate 24. The cooling plate 24 includes a plurality of plates which are arranged in the vertical direction. The outside air blown into the sample storage 2 through the outside air outlet of the outside air introduction unit 40 flows downward along the cooling plate 24.

The cooling plate 24 may only be arranged in a direction that is perpendicular to the flow of the outside air blown into the sample storage 2 through the outside air outlet of the outside air introduction unit 40 in this manner.

In the embodiment illustrated in FIG. 3, a guide plate 54 is further provided. The guide plate 54 directs the outside air blown into the sample storage 2 through the outside air outlet to the cooling plate 24. The guide plate 54 may be a flat plate that faces the inner wall of the sample storage 2 with the cooling plate 24 interposed therebetween. In this embodiment, the guide plate 54 also includes flat plates on the respective sides of the flow of the outside air to thereby constitute a duct together with the inner wall of the sample storage 2, the duct housing therein the cooling plate 24. Such a guide plate 54 can forcibly direct the outside air blown into the sample storage 2 through the outside air outlet of the outside air introduction unit 40 to the cooling plate 24. As a result, it is possible to efficiently allow moisture contained in the outside air to condense on the cooling plate 24.

What is claimed is:

1. A sample cooling device comprising:
   a sample storage storing a sample rack in the sample storage, the sample rack holding a sample container in which a sample is put;
   a first temperature regulation mechanism including a first heat transfer member arranged at a position in contact with the sample rack stored in an inside of the sample storage and a first cooler cooling the sample rack to a temperature equal to or lower than a room temperature through the first heat transfer member;
   a second temperature regulation mechanism including a second heat transfer member arranged at a position separately from the first heat transfer member in the inside of the sample storage and a second cooler cooling the inside of the sample storage to a temperature equal to or lower than the room temperature through the second heat transfer member; and
   a condensate discharge mechanism including a condensate collection tray arranged at a position for collecting condensate condensing on the second heat transfer member and a channel for discharging the condensate collected in the condensate collection tray to an outside of the sample storage,
   wherein an internal space of the sample storage is not sealed due to the existence of a leak path located between the inside and the outside of the sample storage for air to flow from the inside of the sample storage to the outside of the sample storage, the leak path including at least the channel,
   the sample storage includes an outside air introduction unit, the outside air introduction unit forcibly blowing outside air into the internal space so that a pressure inside the sample storage becomes higher than a pressure outside of the sample storage, and
   the outside air introduction unit includes an outside air outlet, wherein the outside air outlet is located inside the sample storage, the position and the direction of the outside air outlet being set so that the outside air blown into the sample storage through the outside air outlet directly heads for the second heat transfer member.

2. The sample cooling device according to claim 1, further comprising:
   a sample inlet of an analyzer;
   a sampling needle sucking a sample from the sample container held in the sample rack and injecting the sample into the sample inlet; and
   a cleaning liquid discharge port for discharging a cleaning liquid through the cleaning liquid discharge port, wherein the cleaning liquid was used for cleaning the sampling needle, the sample inlet, the sampling needle, and the cleaning liquid discharge port being arranged inside the sample storage,
   wherein the sampling cooling device constitutes a sample injection device, and
   the leak path also includes an outlet of the cleaning liquid discharge port.

3. The sample cooling device according to claim 1, further comprising a guide plate, the guide plate directing the outside air blown into the sample storage through the outside air outlet to the second heat transfer member.

4. The sample cooling device according to claim 1, wherein the second heat transfer member comprises a plurality of metal plates, the plurality of metal plates being arranged in parallel to a flow of the outside air blown into the sample storage through the outside air outlet.

5. The sample cooling device according to claim 1,
   wherein the first cooler and the second cooler are Peltier elements, and
   wherein the sample cooling device further comprises heat dissipation fins and air feeding mechanisms for feeding air for heat dissipation to the respective heat dissipation fins;
and wherein the heat dissipation fins and the air feeding mechanisms are provided outside the sample storage for the respective Peltier elements, and either one of the air feeding mechanisms also serves as a mechanism for blowing the outside air in the outside air introduction unit into the internal space.

* * * * *